United States Patent [19]
Horlbeck

[11] Patent Number: 6,061,636
[45] Date of Patent: May 9, 2000

[54] TECHNIQUE FOR REPRESENTING COMBINATORIAL CHEMISTRY LIBRARIES RESULTING FROM SELECTIVE COMBINATION OF SYNTHONS

[75] Inventor: Eric Horlbeck, Plainsboro, N.J.

[73] Assignee: Pharmacopeia, Inc., Cranbury, N.J.

[21] Appl. No.: 08/812,417

[22] Filed: Mar. 6, 1997

Related U.S. Application Data

[63] Continuation-in-part of application No. 08/605,464, Feb. 26, 1996, Pat. No. 5,880,972.

[51] Int. Cl.⁷ .................................................. G01N 35/00
[52] U.S. Cl. ............................... 702/22; 702/27; 702/30; 702/32; 395/500.32
[58] Field of Search .................................. 702/22, 23, 27, 702/30–32, FOR 115–FOR 119; 364/528.01, 528.03, 528.04, 578; 435/6, 7.94, 7.1; 436/56, 43; 422/187–189, 141; 530/333, 334; 536/25.3, 25.31, 25.32–25.34; 434/278, 279, 281; 700/266, 268, 269; 395/500.32

[56] References Cited

U.S. PATENT DOCUMENTS

| | | | |
|---|---|---|---|
| 5,463,564 | 10/1995 | Agrafiotis et al. ................. | 364/528.03 |
| 5,565,324 | 10/1996 | Still et al. .................................... | 435/6 |
| 5,573,905 | 11/1996 | Lerner et al. ................................ | 435/6 |
| 5,587,471 | 12/1996 | Cook et al. ............................. | 556/25.3 |
| 5,663,046 | 9/1997 | Baldwin et al. ............................ | 435/6 |
| 5,723,598 | 3/1998 | Lerner et al. .......................... | 536/25.3 |
| 5,770,455 | 6/1998 | Cargill et al. ........................... | 530/334 |

FOREIGN PATENT DOCUMENTS

WO94/08051   4/1994   WIPO .

OTHER PUBLICATIONS

Baldwin, J.J. et al. "Design, Synthesis, and Preparation of An Encoded Small–Molecule Library for A Wide Variety of 96–Well Based Bioassays." vol. 6/No. 1/ 1995/1996 pp. 74–78. (No Month).

Brenner, S. "Encoded Combinatorial Chemistry," Proc. Natl. Sci. USA vol. 89 pp. 5381–5383 Jun. 1992 Chemistry.

Baum, R.M., "Combinatorial Approaches Provide Fresh Leads for Medicinal Chemistry," Chemical & Engineering News, vol. 72, pp. 20–25, Feb. 7, 1994.

Burbaum, J.J. et al., "A Paradigm for Drug Discovery Employing Encoded Combinatorial Libraries," Proc. Natl. Acad. Sci. USA, vol. 92, pp. 6027–6031, Jun. 20,1995.

Baldwin, J.J. et al., "Synthesis of a Small Molecule Combinatorial Library Encoded with Molecular Tags," Journal of the American Chemical Society, vol. 117, No. 20, pp. 5588–5589, 1995. No Month.

Nestler, H.P. et al., "A General Method for Molecular Tagging of Encoded Combinatorial Chemistry Libraries," The Journal of Organic Chemistry, vol. 59, No. 17, pp. 4723–4724, 1994. No Month.

Borchardt, A. et al., "Synthetic Receptor Binding Elucidated with an Encoded Combinatorial Library," Journal of the American Chemical Society, vol. 116, No. 1, pp. 373–374, 1994 (No Month).

Ohlmeyer, M.H.J. et al., "Complex Synthetic Chemical Libraries Indexed with Molecular Tags," Proc. Natl. Acad. Sci. USA, vol. 90, pp. 10922–10926, Dec. 1993.

Longman, R., "The Promise of Combinatorial Chemistry," Windhover's In Vivo The Business & Medicine Report, vol. 12, No. 5, pp. 23–31, May 1994.

(List continued on next page.)

*Primary Examiner*—Hal Wachsman
*Attorney, Agent, or Firm*—Ronald B. Goldstein

[57] ABSTRACT

A computer-implemented method and apparatus are provided for the generation and representation of combinatorial chemical libraries produced by a series of chemical reaction stages, each stage involving a multiplicity of simultaneous chemical reactions utilizing a set of potential synthons. The disclosed method and apparatus are implemented when one or more of the potential synthons are omitted from certain reactions during one or more of the reaction stages.

13 Claims, 16 Drawing Sheets

OTHER PUBLICATIONS

Service, R.F., "Radio Tags Speed Compound Synthesis," Science, vol. 270, p. 577, Oct. 1995.

Martin, E.J. et al., "Measuring Diversity: Experimental Design of Combinatorial Libraries for Drug Discovery," Journal of Medicinal Chemistry, vol. 38, No. 9, pp. 1431–1436, 1995. (No Month).

Domine, D., et al., "A Nonlinear Map of Substituent Constants for Selecting Test Series and Deriving Structure–Activity Relationships. 1. Aromatic Series," Journal of Medicinal Chemistry, vol. 37, No. 7, pp. 973–987, 1994. (No Month).

Abraham, M.H. et al., "Hydrogen Bonding. 32. An Analysis of Water–Octanol and Water–Alkane Partitioning and the $\Delta$log P Parameter of Seiler," Journal of Pharmaceutical Sciences, vol. 83, No. 8, pp. 1085–1100, 1994. (No Month).

Prior Art

Prior Art

R1—R2—R3
    |
    R4

CORE STRUCTURE WHICH CANNOT BE REPRESENTED BY PRIOR ART

Prior Art

Prior Art

| MONOMER STRUCTURE | DAYLIGHT LINEAR REPRESENTATION | USER-ASSIGNED NAME |
|---|---|---|
|  | NC(C)C(=O) | Ala |
|  | NC(CS1)C(=O) | Cys |
|  | NC(C(C)C)C(=O) | Val |

Prior Art

Prior Art

CONTENTS OF
COMBINATORIAL  =  Pam2768.[Brx;Clx;Fx;Hx;Ix]2.
LIBRARY              [Clx;Fx;Hx;Nitrox]7.[Eohx;Etx;
                     Hx;Mcpx;Mex;Mohx;Phex;Ppox;
                     Tfex;Tppx]6.[Carx;Hx;Ohx]8

Pam2768.Brx2.Nitrox7.Mex6.Hx8 ated using combi
TECHNIQUE FOR REPRESENTING COMBINATORIAL CHEMISTRY LIBRARIES RESULTING FROM SELECTIVE COMBINATION OF SYNTHONS This is a continuation-in-part of U.S. application Ser. No. 08/605,464, filed Feb. 26, 1996, U.S. Pat. No. 5,880,972.

TECHNICAL FIELD

This invention relates to combinatorial chemistry, and more particularly, to an improved technique for representing libraries resulting from combinatorial chemistry.

BACKGROUND OF THE INVENTION

This invention relates to a system and method useful for the generation and representation of chemical libraries and, more particularly, to a computer-implemented system and method useful for the generation and representation of combinatorial chemistry libraries.

Combinatorial chemistry allows scientists to generate large numbers of unique molecules with a small number of chemical reactions. Rather than using the traditional approach of synthesizing novel compounds one at a time, compounds are synthesized by performing chemical reactions in stages, and reacting all of the molecules formed in stage n-1 with each reactant in stage n. An example of this process is shown in FIG. 1. While, for purposes of this example, it is assumed that R1–R9 of FIG. 1 represent single reactants which are used to perform single reactions, those skilled in the art will appreciate that any or all of R1–Rn can represent multiple reactions with which different types of chemistry or chemical sequences can be performed.

In stage 1 of the example of FIG. 1, molecules A and B are reacted with reactant R1. Similarly, molecules C and D are reacted with reactant R2, and molecules E and F are reacted with reactant R3 (although only one of each type of molecule is shown in FIG. 1, many of each type are used in the first stage and, consequently, many of each type are formed in subsequent stages). Molecules A–F are the "starting molecules," and the molecules formed after each stage are represented in FIG. 1 by the starting molecule followed by the sequence of reactants separated by colons.

In stage 2, all of the molecules formed in stage 1 are reacted with reactants R4, R5 and R6, and in stage 3, all of the molecules formed in stage 2 are reacted with reactants R7, R8 and R9. As is shown in FIG. 1, this process generates 54 diverse molecules after stage 3, having started with only six molecules and having performed only nine reactions. The diverse library of molecules thus formed may be used to screen for biological activity against a therapeutic target or for any other desirable property.

A general formula for the maximum number of unique molecules which can be formed using a combinatorial process is $$\pi_{j=2}^{N} R_j \left( \sum_{n=1}^{k} m_n \right)$$

where N is the number of stages, R is the number of reactants at stage j, K is the total number of reactants in the first stage, and m is the number of molecules reacted with reactant n. This formula represents the maximum number of unique molecules formed because it is possible for different reaction steps to generate the same compounds.

The following references are related to combinatorial chemistry, and are hereby incorporated by reference in their entirety: PCT International Application Number WO 94/08051, filed Oct. 1, 1993; "Combinatorial Approaches Provide Fresh Leads for Medicinal Chemistry," *Chemical & Engineering News*, Vol. 72, Feb. 7, 1994, pp. 20–26; "A Paradigm for Drug Discovery Employing Encoded Combinatorial Libraries," *Proc. Natl. Acad. Sci. USA*, Vol. 92, pp. 6027–6031, June 1995; "Synthesis of a Small Molecule Combinatorial Library Encoded with Molecular Tags," *Journal of the American Chemical Society*, Vol. 117, No. 20, pp. 5588–5589, 1995; "A General Method for Molecular Tagging of Encoded Combinatorial Chemistry Libraries," *The Journal of Organic Chemistry*, Vol. 59, No. 17, pp. 4723–4724, 1994; "Synthetic Receptor Binding Elucidated with an Encoded Combinatorial Library," *Journal of the American Chemical Society*, Vol. 116, No. 1, pp. 373–374, 1994; "Complex Synthetic Chemical Libraries Indexed with Molecular Tags," *Proc. Natl. Acad. Sci. USA*, Vol. 90, pp. 10922–10926, December 1993; "The Promise of Combinatorial Chemistry", *Windhover's In Vivo The Business & Medicine Report*, Vol. 12, No. 5, May, 1994, pp. 23–31.

When a compound generated using combinatorial chemistry is found to have a desirable property, it is important to be able to determine either the structure of the compound or the manner in which it was synthesized so that it can be made in large quantities. Until recently, combinatorial chemistry was practical only for generating peptides and other large oligomeric molecules because direct structure elucidation for most compounds is problematic, and such large molecules (made of repeating subunits) offered the advantage of being amenable to sequencing to determine their structure. In contrast, only very small libraries of small (i.e., nonoligomeric) molecules could be generated because, since such small molecules cannot be sequenced, the size of the library had to be kept small enough to allow a scientist to keep track of every compound made.

Combinatorially generated peptide libraries proved to be of limited value. Peptides are poor therapeutic agents, in part because of their lack of stability in vivo. Drug companies preferred libraries of small organic molecules which, unlike most large molecules such as peptides, can frequently act when taken orally.

A need therefore existed for a scheme by which the reaction history of small molecules generated using combinatorial chemistry could be tracked. A method was developed for "tagging" the generated compounds with an identifier for each reaction step in its synthesis. The process is called the "cosynthesis" method because, as a compound is synthesized, a tag linked to the compound (or to the solid support, e.g., bead, upon which the compound is being synthesized) by means of a chemical bond is also synthesized, which encodes the series of steps and reagents used in the synthesis of the library element. When a library compound is found to have a desirable property, the tag is sequenced to determine the series of reaction steps which formed the compound. Because the tags must be sequenced, large molecule tags such as oligonucleotides and oligopeptides have been used.

The cosynthesis method has many inherent problems. For example, the tagging structures themselves are necessarily chemically labile and unstable and as such are incompatible with many of the reagents commonly used in small molecule combinatorial chemistry. Additionally, multiple protecting groups are required and the cosynthesis of a tag may reduce the yield of the library compounds. For these reasons, the cosynthesis method has not made small molecule combinatorial chemistry a commercially viable technology.

The assignee of the instant invention has developed a proprietary, pioneering technology which makes small molecule combinatorial chemistry commercially feasible. This technology is fully described in PCT published application number WO 94/08051 and employs binary coding of the synthesized compounds such that only the presence or absence of tags, and not their sequence, defines the compound's reaction history. The operation of the assignee's binary coding system is depicted in FIGS. 2A–2C.

FIG. 2A shows a three-stage combinatorial synthesis with three reactants in each stage. While, as is known, two binary digits can uniquely identify four reactants, in a preferred embodiment, the binary digits 00 are not used to identify a reactant. Consequently, as shown in FIG. 2B, the reaction history of any compound formed in the combinatorial synthesis of FIG. 2A can be represented with a six-digit binary code. The two least significant digits represent the reactant employed in stage 1, the next two digits the reactant employed in stage 2, and the two most significant digits the reactant employed in stage 3. The two digit binary code for each reactant in each stage is shown below the reactant in FIG. 2A, with underlining representing bits contributed by other stages.

As shown in FIG. 2C, then, compound A, which was synthesized with reactants R3, R5 and R9, can be represented with the binary code 111011. Similarly, compound B, which was synthesized with reactants R1, R6 and R8, can be represented with the binary code 101101 and compound C, which was synthesized with reactants R2, R4 and R7, can be represented with the binary code 010110.

Pursuant to the assignee's proprietary tagging technology, each of the bits of the binary code which defines a compound's reaction history is represented by a tagging molecule. These tagging molecules are bound to the solid support as the synthesis progresses such that the presence of a tag indicates that the value of the bit it represents is "1", while the absence of a tag indicates that the value of the bit it represents is "0". As illustrated in FIG. 2B, tag T1 represents the least significant bit, with successive tags assigned to successive bits such that tag T6 represents the most significant bit. As shown in FIG. 2C, then, tags T1, T2, T4, T5 and T6 will be bound to the solid support on which compound A was synthesized, tags T1, T3, T4 and T6 will be bound to the solid support on which compound B was synthesized, and tags T2, T3 and T5 will be bound to the solid support on which compound C was synthesized. While, in a preferred embodiment, the assignee's binary coding technique employs tagging molecules which are bound to the solid support, those skilled in the relevant art will appreciate that the assignee's binary coding technique is not limited to this implementation, and that binary coding can be implemented with any tagging technique including but not limited to radio tagging. Radio tagging is described in "Radio Tags Speed Compound Synthesis," *SCIENCE*, Vol. 270. p. 577, October 1995, which is hereby incorporated by reference in its entirety.

This binary tagging technique overcomes the above referenced disadvantages of the cosynthesis method, making small molecule combinatorial chemistry feasible. As alluded to in the above referenced article titled "The Promise of Combinatorial Chemistry", however, this chemical advance has given rise to a new engineering problem, namely, how to concisely represent the contents of small molecule combinatorial libraries, each potentially containing hundreds of thousands of unique chemical compounds, and how to plan their generation such that the probability of generating compounds with useful characteristics is increased. Existing systems, such as those developed by Tripos, Inc. ("Tripos"), MDL Information Systems, Inc. ("MDL") and Daylight Chemical Information Systems, Inc. ("Daylight") are either infeasible or impractical for use with small molecule combinatorial libraries because the representation schemes implemented by these systems do not allow for concise representations of all types of small molecule combinatorial libraries, for tracking of those libraries which are binary coded or for correct enumerations of those libraries generated on solid support.

In the MDL system, the operation of which is described with reference to FIGS. 3A–3D, a combinatorial library is represented with 1) one core chemical structure having attachment points for chemical moieties which are added or attached to the core structure at each stage of the combinatorial synthesis; and 2) lists of the moieties which can be added to the core structure at each stage ("additions").

An example of an MDL representation of a combinatorial library is shown in FIG. 3A. The core structure is shown with attachment points R1–R4, representing points of attachment for moieties which can be added to the core structure in stages 1–4 of the combinatorial synthesis respectively. Also shown are four lists of structures, each list representing the compounds which can be added to the core structure in one of the four stages. The point of attachment of each compound added to the core structure is indicated with a dot. The contents of the combinatorial library can be enumerated by identifying all permutations of the compounds of the four lists as attached to the core structure. As used in this specification, the term "enumeration" will mean the process of generating representations of the entire structure of each of the compounds in the library based on the concise representation employed by a system.

The MDL system has many limitations which render it infeasible for use with small molecule combinatorial chemistry. For example, each addition can have at most two attachment points. While suitable for peptide chemistry, two attachment points per addition are insufficient to represent the structures contained in many small molecule combinatorial libraries. For example, the MDL system would be unable to represent a core structure such as that shown in FIG. 3B, since the moiety R2 has three points of attachment.

Another limitation of the MDL system which makes it infeasible for use with small molecule combinatorial chemistry is that all the possible additions at each reaction stage must attach at the same point or points on the core structure. It is possible in small molecule combinatorial synthesis to have different additions at a given reaction stage which attach at different points on the structures generated in previous stages.

Furthermore, the MDL system cannot represent additions which attach only on a subset of the structures formed in previous reaction stages. An example of such a library is shown in FIG. 3C, where a core structure of a combinatorial library can be seen along with a subset of the additions possible from stages 1 and 2. Since the first addition from stage 2 attaches only if the second addition from stage 1 attaches, the MDL system could not represent the library, since all additions from all stages must attach directly to the core structure in the MDL system. Since substituents from a given stage may or may not attach depending on the identities of the substituents attached during previous stages, this limitation also renders the MDL system unsuitable for use with small molecule combinatorial chemistry.

Finally, there are many ways in which small molecule combinatorial libraries can be generated for which a single core structure cannot be defined and which, consequently, cannot be represented by the MDL system. For example, if the possible additions at each of the first three stages are as shown in FIG. 3D, where the black boxes are used to represent chemical structures and the numbered bonds represent points of attachment, the MDL system could not represent the library. No single core structure can be defined to which all the possible additions from all the stages attach. Rather, in the example of FIG. 3D, two core structures are required, depending on whether the first or the second addition from R2 attaches to the addition from R1.

The Tripos system is similar in many respects to the MDL system, and is similarly incapable of concisely representing all types of small molecule combinatorial libraries. For example, like the MDL system, the Tripos system requires that a common core structure be defined, and like the MDL system, it cannot handle combinatorial chemistry where additions attach only to a subset of the structures formed in previous stages. Although in some respects the Tripos system is more flexible than the MDL system (e.g. all additions from all stages need not link directly to the core), it is in many respects even more limiting than the MDL system. For example, the core structure of the Tripos system must be well defined in that it cannot be made up of all variables. This severely limits the types of chemistry with which it can be used because, as discussed above, defining a core structure can be problematic. In short, for many of the same reasons discussed with respect to the MDL system, it is infeasible to use the Tripos system as a tool for representing the contents of small molecule combinatorial chemistry libraries.

The Daylight system, while purportedly designed to represent combinatorial libraries, does not solve the problem of concisely representing small molecule libraries in such a way that a chemist, from the concise representation alone, can understand the makeup of the library. In order to represent the contents of these libraries concisely, Daylight employs several levels of indirection, meaning the "concise" representation is actually useful only as an index into a database from which the contents of the library can ultimately be discerned. The operation of the Daylight system is illustrated in FIGS. 4A–4E.

In the Daylight system, monomers are assigned arbitrary names by the user, and are represented and stored in the system using a linear representation of the atoms of the monomer as demonstrated in FIG. 4A. The atoms are listed in the linear representation in the order in which they bind, with branches indicated in parentheses. Atoms to which other monomers bind, or which serve as the point of a ring closure on the monomer, are labeled with numbers appearing to the immediate right of the atom. When the final polymerized structure is enumerated, paired number labels internal to the monomer definition will be bound together first, after which like labels will be bound together from left to right in the order in which they appear. Because each monomer is independently defined, and it is impossible to know a priori the location in the polymerized structure at which any atom will bind, each monomer contains number labels from 1–N, and the representation scheme for the polymerized structure provides for substitution of these labels with labels indicating the attachment points in the polymerized structure. FIG. 4A shows the chemical structure for three monomers, the manner in which they are represented with the Daylight linear representation scheme, and arbitrary names which can be assigned to the monomers by the user. The sulfur atom in the "Cys" monomer has a label of 1. Since no other atom in Cys is labeled with a 1, which would indicate points for a ring closure, the sulfur atom can serve as a point of attachment to other monomers.

FIG. 4B demonstrates how a polymerized molecule can be represented in the Daylight system using linked monomer names. Also shown in FIG. 4B is the Daylight linear representation of these linked monomers, and the actual chemical structure of the polymerized molecule represented. Note that while the sulfur of every Cys monomer is not required to serve as a point of attachment, the two that do are bound at the sulfurs with like labels of "1".

FIGS. 4C and 4D present a more detailed example of the way monomers are represented in the Daylight system. FIG. 4C illustrates the way five monomers are represented by Daylight's linear representation scheme and arbitrary user-assigned names for each. The first monomer of FIG. 4C shows both ring binding indicators, which occur in pairs (the numbers 7, 8 and 9 in the first structure of FIG. 4C, indicated in grey), and unpaired numbers indicate points of attachment with other monomers (the numbers 1–4 in the first structure of FIG. 4C, indicated in underlining). As can be seen with respect to this monomer, which has been named "Pam" by the user, a lower case "c" represents a carbon of an aromatic ring and an upper case "C" represents a carbon of a non-aromatic ring. Single atom monomers do not require labels to indicate that they can serve as points of attachment, since they have only one possible point of attachment.

FIG. 4D demonstrates how the contents of a combinatorial library can be represented as a string of monomer names separated by periods (additional monomers, besides those defined in FIG. 4C, are used for purposes of the example). Monomer names followed by numbers in a polymerized compound or library definition indicate, by their order, the numbers which should be substituted for the numbers in the monomer definition. Thus, "Pam2768" indicates that the number in the first position following the monomer name, "2", should be substituted for the number "1" in the monomer Pam. Similarly, the number in the second position following the monomer name, "7", should be substituted for the number "2" in the monomer Pam, and so on. The identities of possible additions "2", "7", "6" and "8" are listed in brackets before each of the respective numbers. FIG. 4E shows a Daylight representation of a partial enumeration of the library of FIG. 4D, as well as the chemical structure it represents.

As is intuitively clear, a scientist could not look at a library representation such as Pam2768. [Brx;Clx;Fx;Hx;Ix]2. [Clx;Fx;Hx;Nitrox]7. [Eohx;Etx;Hx;Mcpx;Mex;Mohx;Phex;Ppox;Tfex; Tppx]6. [Carx;Hx;Ohx]8 and obtain a conceptual understanding of the contents of the library. To obtain such an understanding of the library, the scientist would have to:

1) Index the database to determine the linear representations for each of the linked arbitrary monomer names in the library representation;
2) Draw out the chemical structure of the monomers represented by each linear representation; and
3) Substitute the number labels in the library definition for the number labels in the monomer definition.

The Daylight system also has some of the same deficiencies as do the MDL and Tripos systems. For example, it is incapable of representing substituents which attach only on a subset of the structures formed in previous reaction stages. When substituents do not attach, the Daylight system will nevertheless show the unattached substituents as distinct members of the enumerated library, which is particularly unsuitable for use with the assignee's binary coding tagging technology as used with solid phase synthesis, wherein all unattached molecules are washed away and do not become part of the library. Additionally, neither the Daylight system nor the MDL or Tripos systems provide facilities for keeping track of small molecule combinatorial libraries generated with binary coding.

Planning the design of a library with molecules having desired characteristics has also proven to be difficult because there exists no computationally feasible deterministic method for selecting starting molecules and reactants with which a diverse small molecule combinatorial library having such characteristics will be created. The manner in which synthons (starting molecules and reactants collectively may be referred to as "synthons") are generally selected, and the limitations therewith, are detailed in U.S. Pat. No. 5,463,564 to Agrafiotis et al., issued on Oct. 31, 1995 (the "'564 patent"), which is hereby incorporated by reference in its entirety. The solution described in the '564 patent involves iteratively:

1) robotically synthesizing "directed diversity" chemical libraries;
2) analyzing the compounds created in step (1);
3) storing structure-activity data for the compounds created;
4) comparing the structure-activity data for the compounds created with those desired for the library;
5) assigning rating factors to the synthons based on how close the generated library is to the desired library;
6) analyzing the structure-activity data to select which synthons will produce libraries with properties closer to the desired library; and
7) generating computer instructions such that the next iteration will utilize the synthons selected in step (6).

There are many drawbacks with the system described in the '564 patent, including but not limited to the following:

1) chemical libraries must be generated repeatedly, a process which may be impractical based on the limited availability of the necessary compounds and reactants. To the extent it is feasible, the process will be very expensive, particularly in light of the fact that many synthons which ultimately may turn out to be superfluous will be required;
2) it is not especially useful with combinatorial chemistry, but rather implements what is explicitly described as a different process altogether, namely "directed diversity" chemistry (Col 5 lines 1–22);
3) it does not describe a solution useful with small molecule chemistry, but rather states that "[t]o date, most work with combinatorial chemical libraries has been limited only to peptides and oligonucleotides . . . " (Col 2 lines 32–34) and that "[t]he peptide synthesis technology is preferred in producing the directed diversity libraries associated with the present invention"; and
4) while a computer is described for evaluating the characteristics of the library generated vis-a-vis the desired library, no scheme is contemplated or described for graphically representing the contents of the generated library such that a scientist could quickly understand exactly what compounds were produced.

It is also highly questionable whether a system such as that described in the '564 patent could actually be built.

The following articles, each of which is hereby incorporated by reference in its entirety, also describe methods for selecting starting molecules and/or criteria used in their selection: "Measuring Diversity: Experimental Design of Combinatorial Libraries for Drug Discovery," *Journal of Medicinal Chemistry*, Vol. 38, No. 9, pp. 1431–1436, 1995 by Martin et al.; "A Nonlinear Map of Substituent Constants for Selecting Test Series and Deriving Structure-Activity Relationships. 1. Aromatic Series," *Journal of Medicinal Chemistry*, Vol. 37, No. 7, pp. 973–987, 1994; "Hydrogen Bonding. 32. An Analysis of Water-Octanol and Water-Alkane Partitioning and the $\Delta$log P Parameter of Seller," *Journal of Pharmaceutical Sciences*, Vol. 83, No. 8, pp. 1085–1100, 1994. However, none of these references describe an automated or semi-automated system for use with combinatorial chemistry or, for that matter, the application of evaluation criteria to a proposed combinatorial library.

There is, therefore, a need for a system and method which provides a concise and accurate representation of the contents of actual or planned small molecule combinatorial libraries created with solid phase synthesis. Additionally, there is a need for a system and method useful for planning the development of small molecule combinatorial libraries. Finally, there is a need for a system and method which combines these two capabilities such that synthons can be automatically and intelligently selected, and the library which would be combinatorially created therewith evaluated such that the results of the evaluation add to the intelligence with which synthons will be selected in the future.

SUMMARY OF THE INVENTION

It is an object of the present invention to provide a concise representation of the contents of any combinatorial chemical library.

It is another object of the present invention to produce an accurate enumeration of the contents of any combinatorial chemical library generated on solid support.

It is another object of the present invention to provide a tool for tracking the contents of any combinatorial chemical library labeled with binary coding.

It is another object of the present invention to provide a combinatorial chemical library planning tool for automatically and intelligently selecting synthons without performing a chemical synthesis.

It is another object of the present invention to provide a combinatorial chemical library planning tool for automatically and intelligently selecting synthons without performing a chemical synthesis, and thereafter automatically generating a concise representation of the combinatorial library which would be created therewith.

It is another object of the present invention to provide a combinatorial chemical library planning tool for automatically and intelligently selecting synthons without performing a chemical synthesis, automatically generating a representation of the combinatorial library which would be created therewith, evaluating this representation and improving the intelligence with which synthons are selected as a function of this evaluation.

It is another object of the present invention to provide a combinatorial chemical library planning tool for automatically and intelligently selecting synthons without performing a chemical synthesis, automatically generating a representation of the combinatorial library which would be created thereby, automatically evaluating this representation and improving the intelligence with which synthons are selected as a function of this evaluation.

Further objects and advantages of the present invention will be clear to those skilled in the art from the ensuing detailed description.

DETAILED DESCRIPTION

While the instant invention is described with particular reference to libraries of small molecules, it will be understood that the invention is useful with all combinatorial libraries including, but not limited to, libraries in which additions or contributions can have more than two attachment points. The same features which make the invention particularly useful for small molecule combinatorial chemistry are advantageous for use with all types of combinatorial chemistry.

One object of the present invention is to provide a concise representation of small molecule combinatorial libraries. An example of the use of our invention for this purpose is shown in FIGS. 5A–5E.

Figure 1:
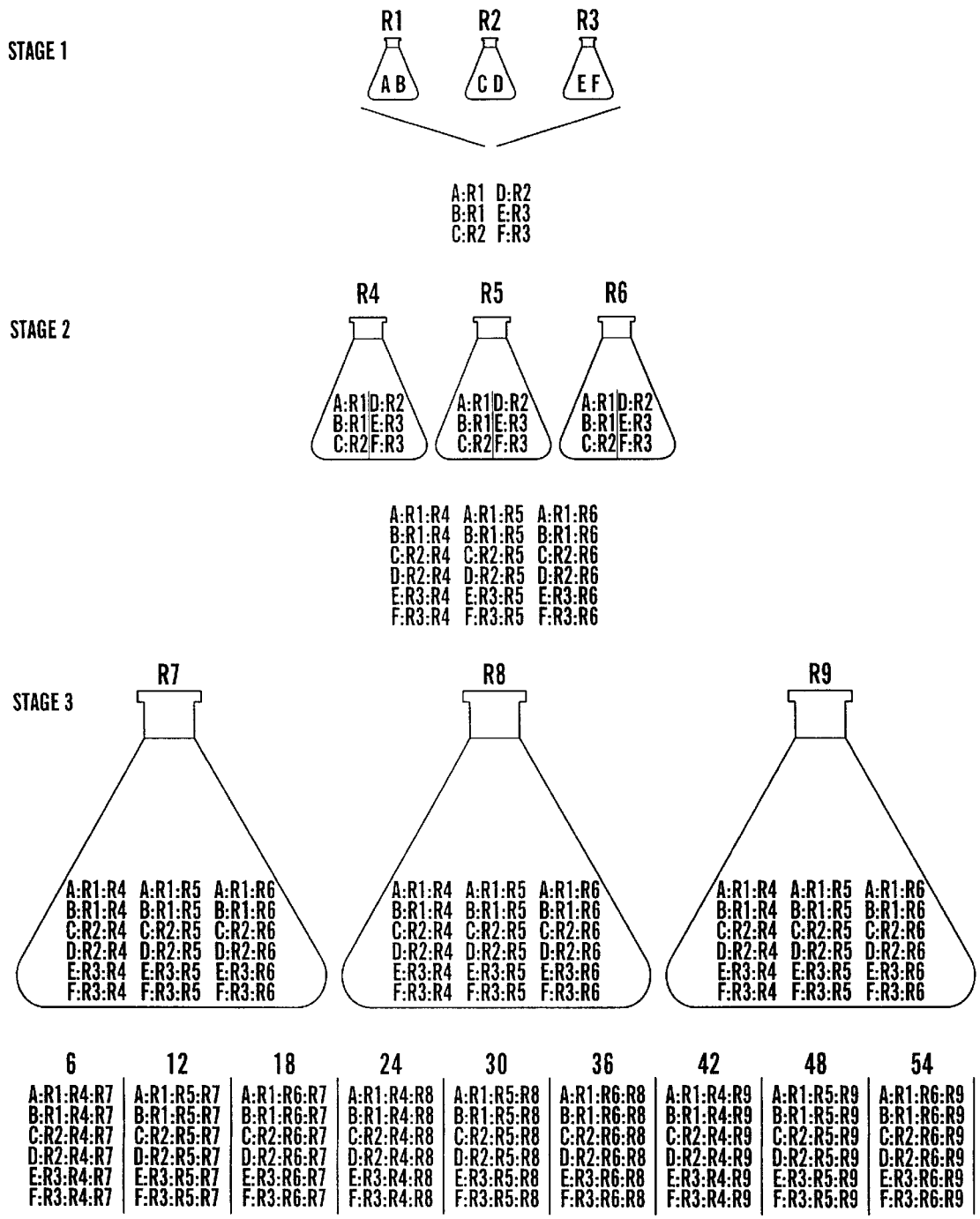
FIG. 1 illustrates the manner in which combinatorial chemistry allows for a large library of diverse molecules to be generated with a small number of reaction steps.
Figures 2A, 2B, 2C:
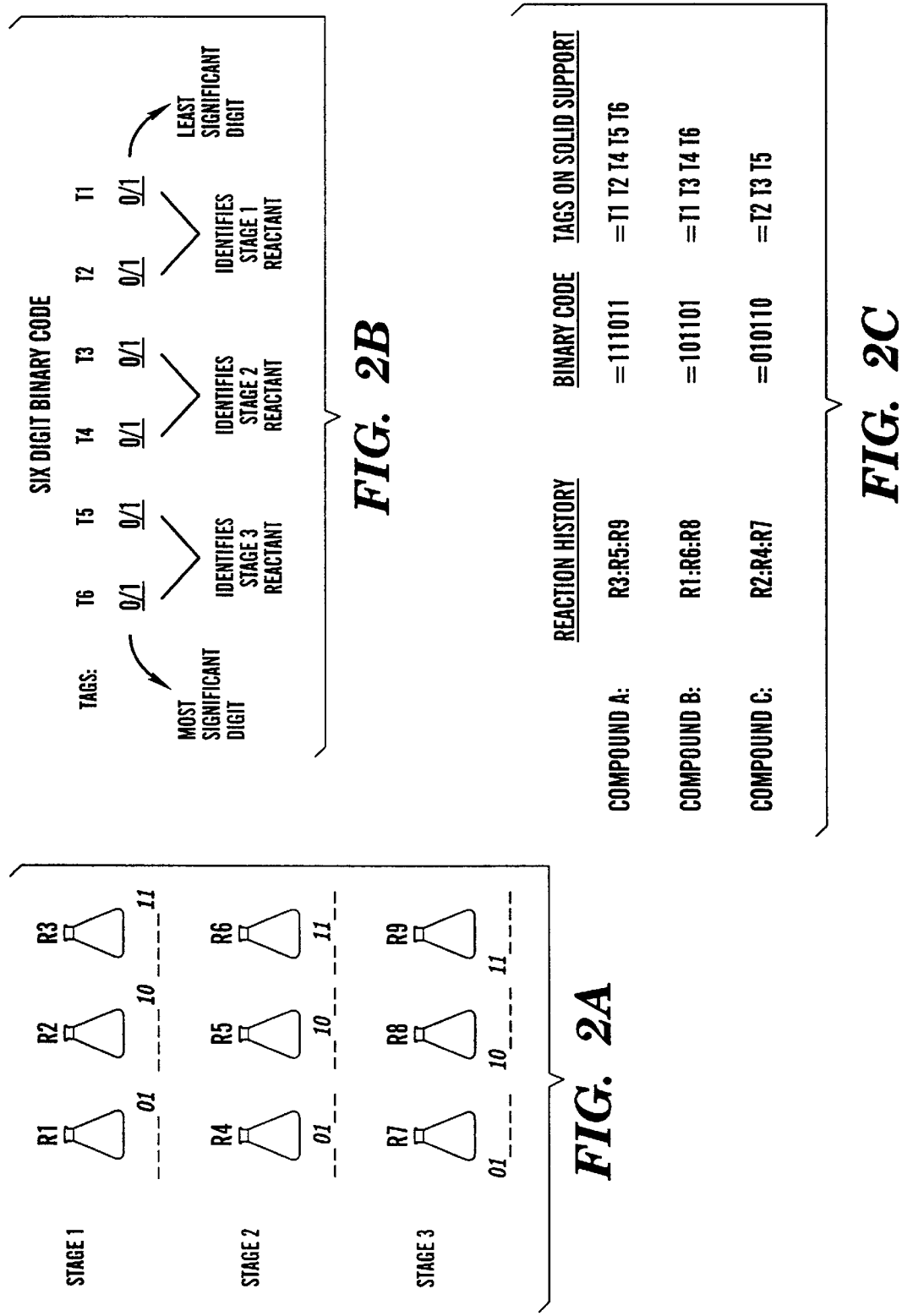
FIGS. 2A–2C illustrate the assignee's proprietary binary coding technology.
Figure 3A:
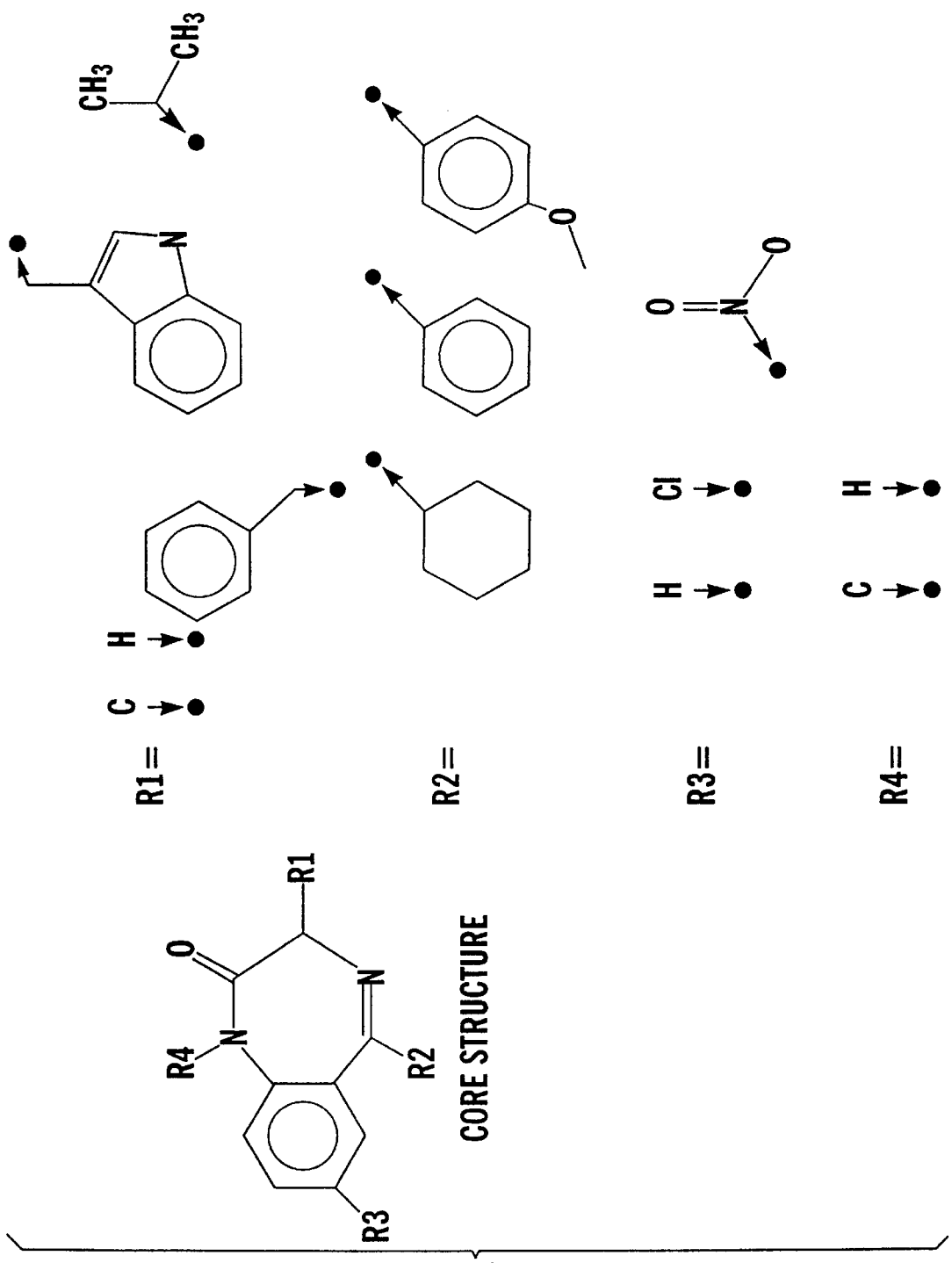
FIGS. 3A–3D illustrate the manner in which the MDL system operates.
Figures 3B, 3C:
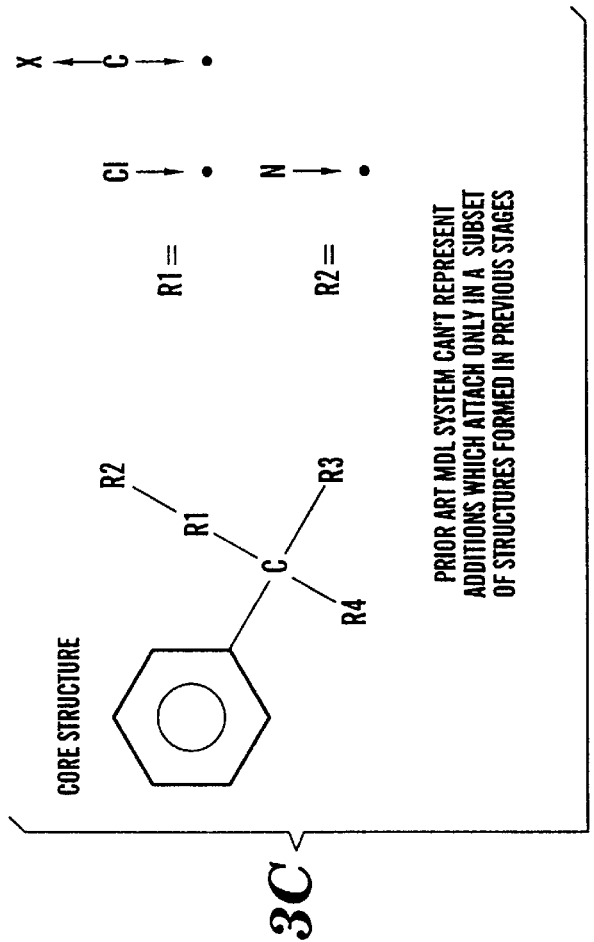
Figure 3D:
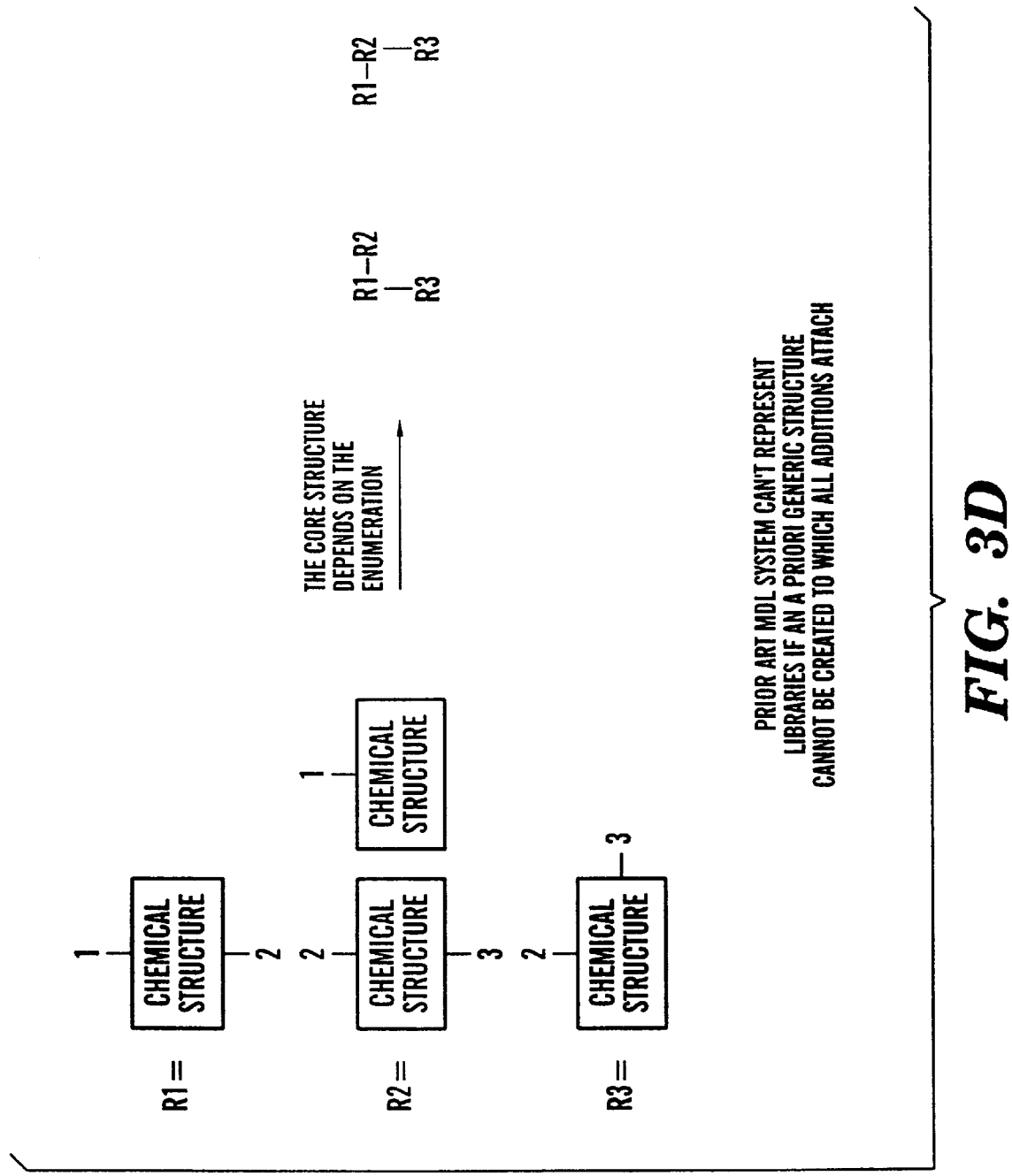
Figure 4A:
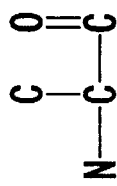
FIGS. 4A–4E illustrate the manner in which the Daylight system operates.
Figure 4A:
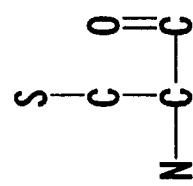
Figure 4A:
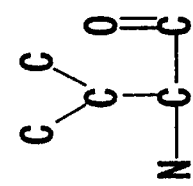
Figure 4B:
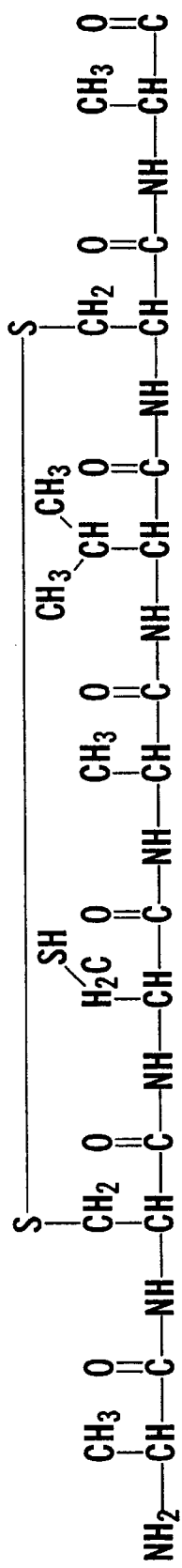
Figure 4C:
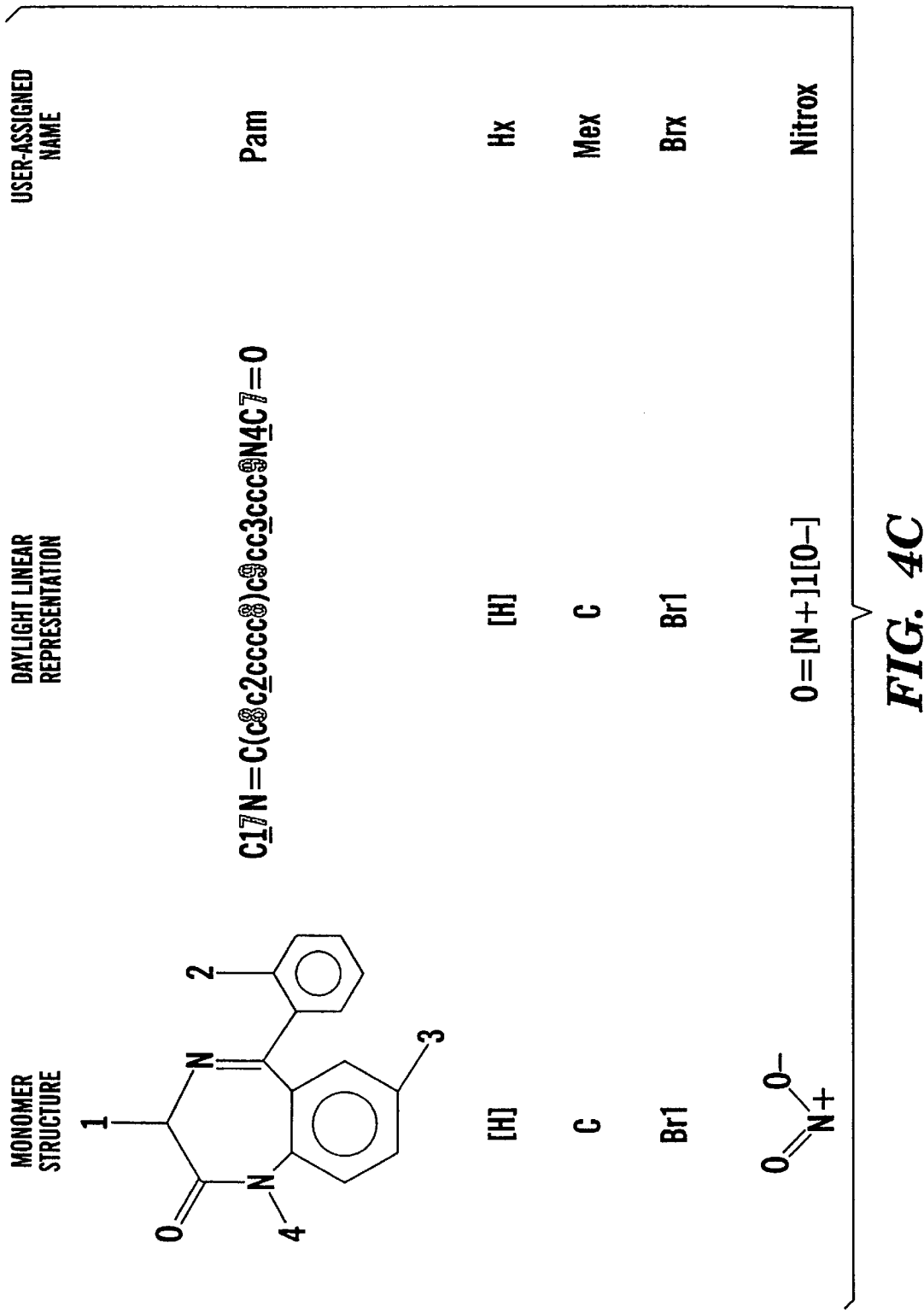
Figures 4D, 4E:
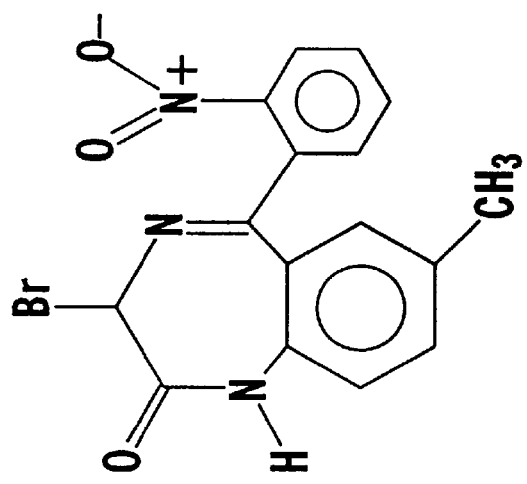
Figure 5A:
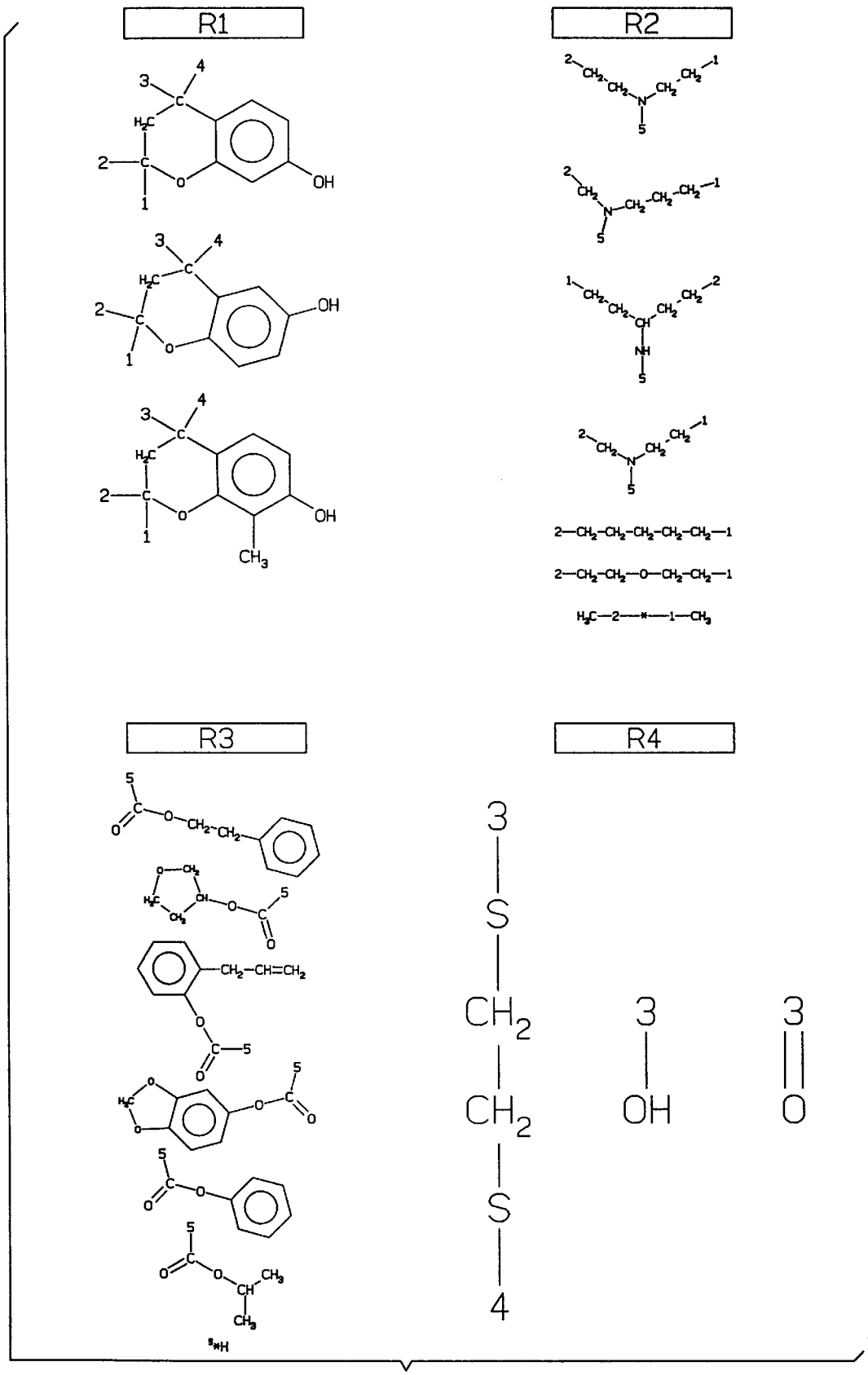
FIGS. 5A–5E illustrate a preferred embodiment of two representations of a small molecule combinatorial library pursuant to the instant invention.
Figure 5B:
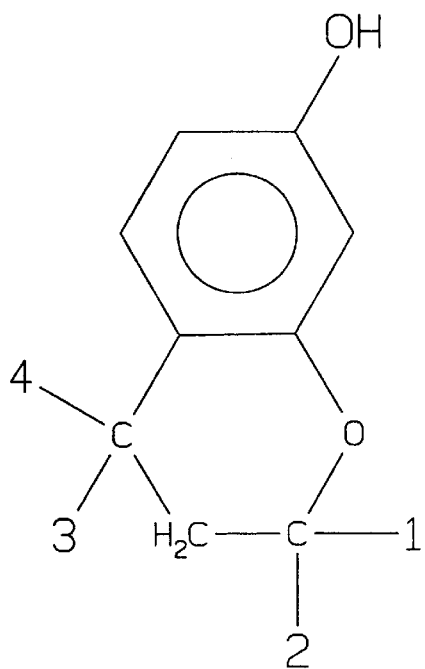
Figure 5B:
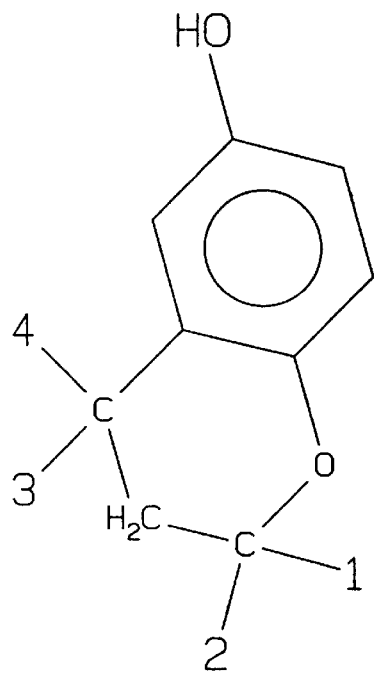
Figure 5B:
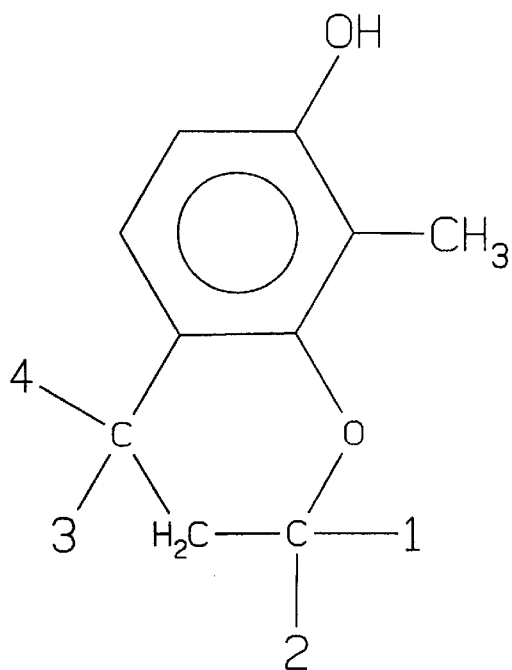
Figure 5C:
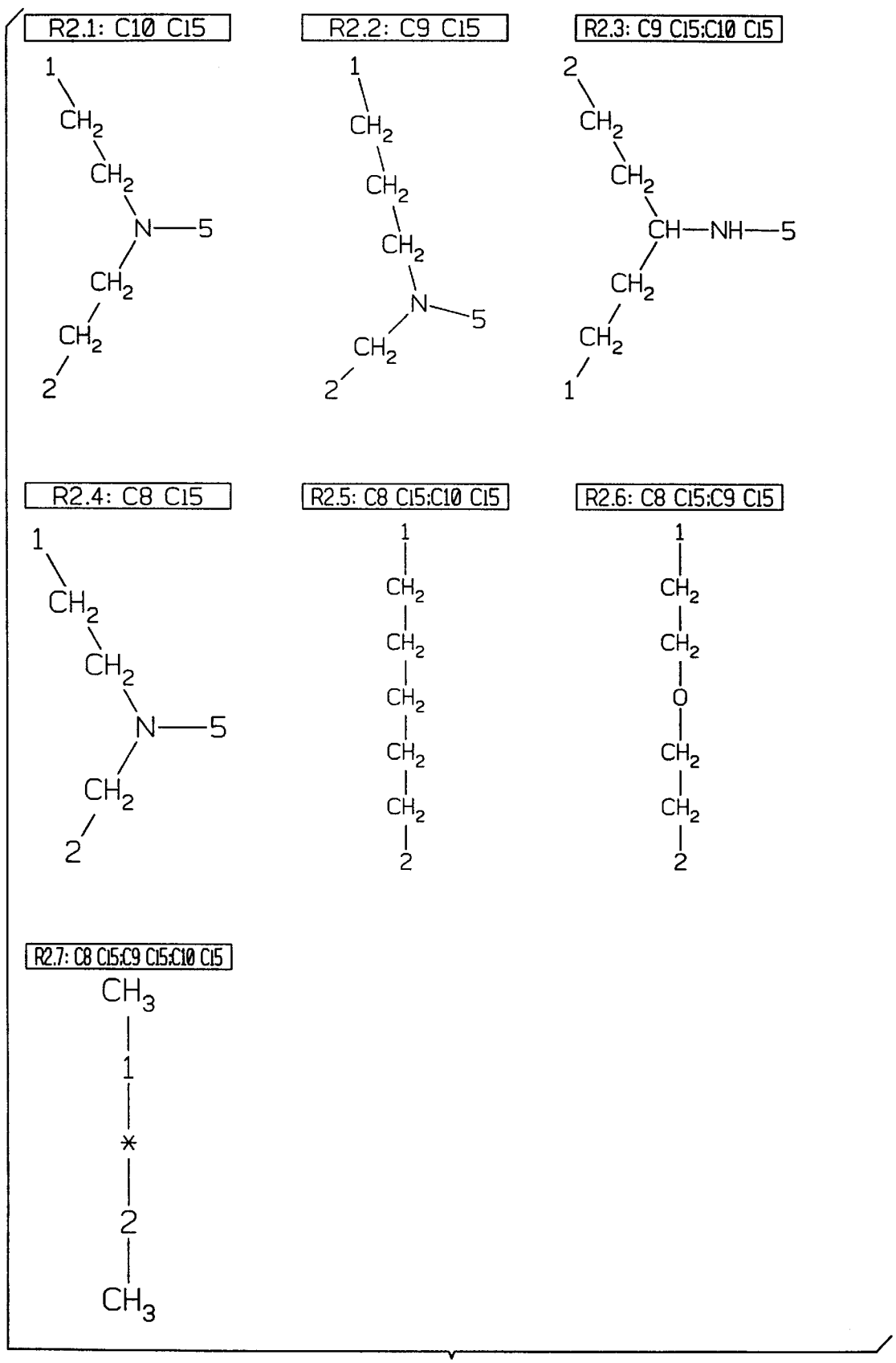
Figure 5D:
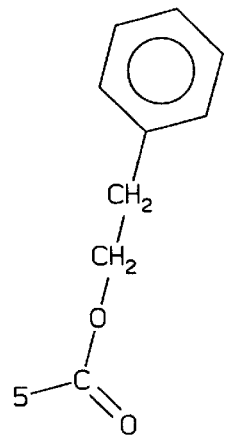
Figure 5D:
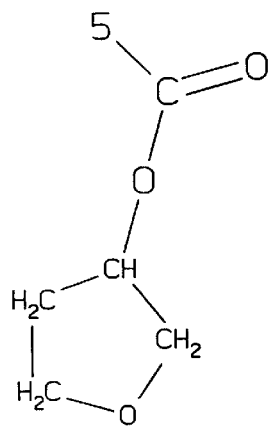
Figure 5D:
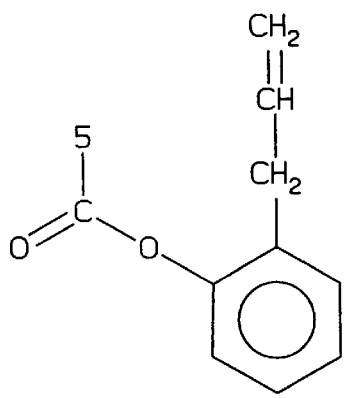
Figure 5D:
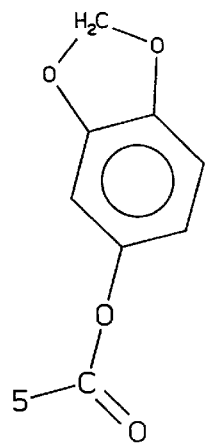
Figure 5D:
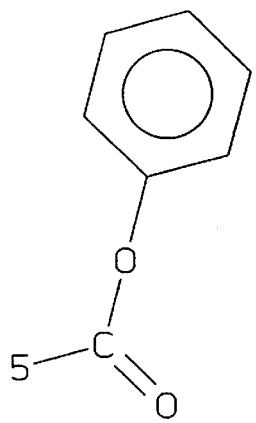
Figure 5D:
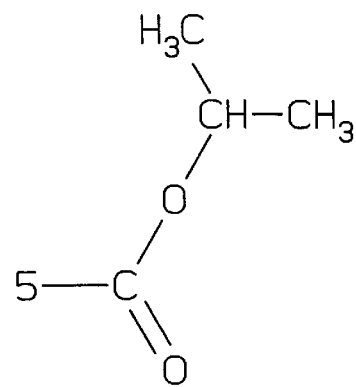
Figure 5D:
Figure 5E:
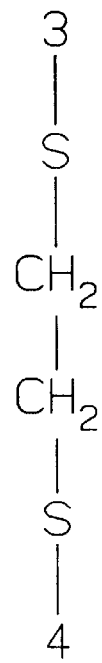
Figure 5E:
Figure 5E:
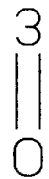

R1–R4 in FIG. 5A represent four reaction stages. The chemical structures shown for each stage represent the contributions made by the synthons utilized in that stage, i.e., the portion of each synthon ultimately incorporated into a member of the library, as well as the manner in which these contributions can be pieced together with the contributions of the other stages. In this way, our system differs markedly from the MDL and Tripos systems, as those systems begin with a single core structure, while our representation allows for an unlimited number of contributions in the first step to accurately reflect the manner in which the library compounds are synthesized. The contribution would not include, for example, portions of the synthon which react to form by-products that are "washed away" during the synthesis process. Every structure of R1 is combined with every structure of R2 (as long as there is a place for the respective structures to attach to one another, as will be explained below). Every resulting structure R1+R2 is combined with every structure of R3, and every structure R1+R2+R3 thereby created is combined with every structure of R4 (again, as long as there is a place for the respective structures to attach to one another). The structures R1+R2+R3+R4 thus created represent the library of molecules combinatorially formed.

The manner in which structures are combined is indicated by like labels, in a preferred embodiment like numbers, in the structures. The numbers label the bonds themselves. For example, the first structure of R1

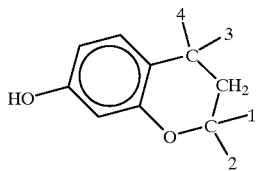

may be combined with the first structure of R2

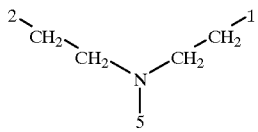

at numbers "1" and "2" (i.e., the two labels which are identical in the two structures of R1 and R2 under discussion) to form

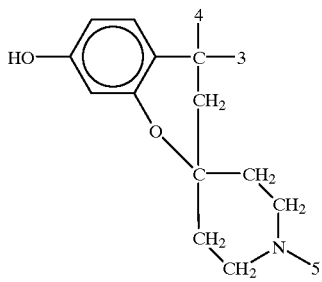

The numbers 3, 4 and 5 are labels used to indicate the positions at which the particular structure R1+R2 under discussion may combine with the contributions of stages R3 and R4.

It is readily apparent that this representation overcomes the limitations described above with respect to the MDL, Tripos and Daylight systems. For example, no single "core" structure is required, substituents can have any number of attachment points, and substituents from later stages can attach at any point on structures from previous stages. In addition, this present method of concisely representing the contents of small molecule combinatorial libraries does not employ indirection, making it possible for a scientist to view the contents of the entire library without the need for any cross-referencing. This aspect of our invention can be implemented using commercially available packages for representing chemical structures, or can be routinely implemented using conventional programming techniques by those having ordinary skill in the relevant art. In any case, this aspect of our invention is directed to the manner in which the library is represented and not to any particular implementation of the representation scheme.

In an additional embodiment of the invention, our representation technique takes into account the fact that certain reaction products from certain stages of the reaction may not be combined with certain of the synthons in the next stage. The combination may be impossible (e.g., because the reaction will not occur) or simply undesirable (e.g., because such reaction products are intended to be excluded from the library).

The latter situation contrasts with combinatorial chemistry techniques generally utilized today which, in their most elementary form, mix every molecule formed during reaction stage N with every synthon from reaction stage N+1. However, as will be more fully described hereafter, in certain instances, it is desirable or possible to mix with the synthons of reaction stage N+1 only some of the molecules formed during reaction stage N. Alternatively, it may be desirable or possible to mix all molecules formed during reaction stage N with only some of the synthons of reaction stage N+1. In general, some or all synthons from any reaction stage (other than the very first reaction stage) may be combined with some or all of the products from any previous reaction stage, and certain reaction steps can be omitted. We term these situations "selective combination."

In order to more accurately represent and track molecules generated combinatorially via selective combination, an additional improvement to the present invention has been developed. A technique has been developed to tag, track, and represent combinatorial libraries, and enumerate the resulting chemical structures, which easily and compactly conveys and records the selective combination (e.g., the omitted reaction steps).

In addition to recording and conveying information regarding the omitted reaction steps, our technique allows for the generation and representation of what we term biased libraries. Specifically, it may be desirable to divide the synthons of a reaction stage into subsets, and to then react different proportions of the products of a previous reaction stage with each subset. For example, if reaction stage 2 is divided into two subsets of synthons, it may desirable to react 80% of the products from reaction stage 1 with the first subset of synthons from R2, while reacting only 20% of the products from reaction stage R1 with the remaining subset from reaction stage R2.

The foregoing technique allows the biasing of particular reaction stages. The technique is useful in that the scientist may desire to generate more products containing certain synthons than containing other synthons. In the foregoing example, more products will be generated which result from combinations of the contributions from R1 with the synthons in the first set of R2 (with which 80% of R1 contributions are reacted) than will be generated as a result of combinations between the contributions of R1 and the second subset of R2 (with which only 20% of R1 contributions are reacted).

It is also within the scope of the invention to use such biasing to create a more equal distribution of final products in some cases where certain synthons or products may have been present in disparate proportions. For example, if, stage R1 includes $33\frac{1}{3}\%$ R1.1 and $66\frac{2}{3}\%$ R1.2, equal distribution may be obtained through the use of biasing. Presuming stage R2 is divided into two subsets, the first of which reacts with R1.1, and the second of which reacts with R1.2, twice as much R1 would be reacted with the first subset of R2 as would be reacted with the second subset of R2. This would equalize the amount of the resulting compositions.

Figure 5F:
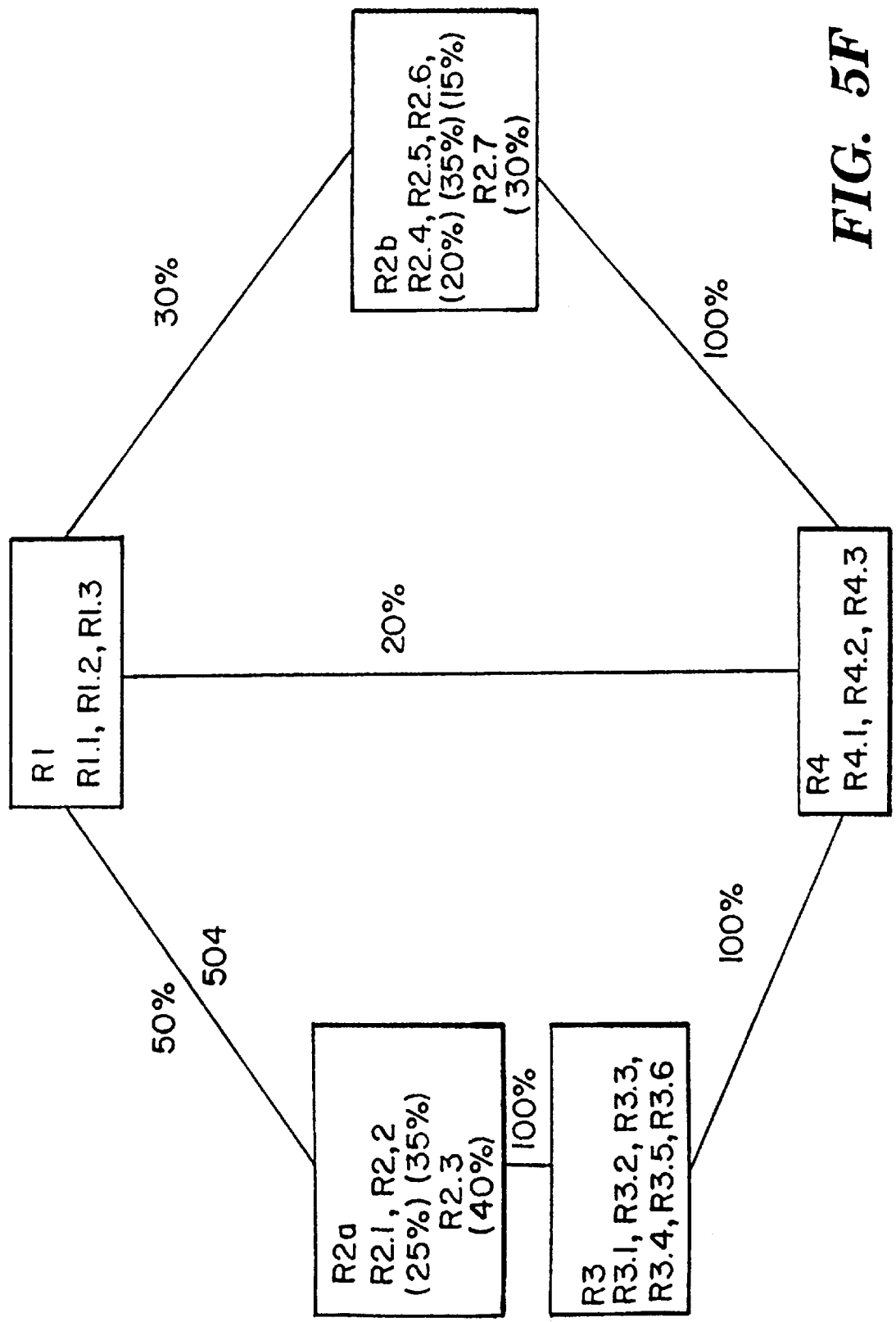
FIG. 5F represents an alternative embodiment of the present invention which includes selective combination, as that term is defined hereafter.

FIG. 5F shows one embodiment of the novel representation scheme to represent and track the generation of a combinatorial library produced via selective combination of contributions from the four stages of FIG. 5A. As can be appreciated from FIG. 5F, the technique immediately and conveniently conveys the fact that all of the products of reaction stage R1 are pooled and then divided into aliquots of 50%, 30%, and 20%. The 50% aliquot is further divided into portions of 25%, 35%, and 40% which, respectively, are reacted with the synthons corresponding to the contributions R2.1, R2.2, and R2.3 in stage R2 to form structures R1.1R2.1, R1.1R2.2, R1.1R2.3, R1.2R2.1, R1.2R2.2, R1.2R2.3, R1.3R2.1, R1.3R2.2, and R1.3R2.3. All of these structures are then reacted with all the contributions in stage R3, and the resulting products are all reacted with all of the contributions in stage R4.

The 30% aliquot from stage R1 is reacted with the synthons corresponding to the contributions R2.4, R2.5, R2.6, and R2.7 in stage R2. (As indicated in FIG. 5F, 20% of such aliquot is reacted with R2.4; 35% of such aliquot is reacted with R2.5; 15% of such aliquot is reacted with R2.6; and 30% of such aliquot is reacted with R2.7). The resulting structures are not reacted with any of the contributions from stage R3, but are reacted directly with the contributions from stage R4. Finally, the 20% aliquot from stage R1 is not reacted with any contributions from either stage R2 or R3, but is reacted directly with all the contributions from stage R4.

From the foregoing it is clear that reaction stage R2 is divided into subsets of synthons. Each distinct subset will have a reaction history different from that of other distinct subsets. When a computer is tracking or representing the library generated by the reactions shown in FIG. 5F, the computer may be programmed to associate certain tagging molecule(s), respectively, with each synthon in each reaction stage. By checking for the presence or absence of tags from a particular reaction stage, the computer can reconstruct the reactions which actually occurred according to the representation in FIG. 5F, and can ultimately determine both the structures of the resulting molecules as well as the procedure for generating these.

Additionally, the biasing technique previously discussed is shown in FIG. 5F, and may be represented with the novel technique as well. Between each subset of contributions and a subsequent subset of contributions with which said subset will combine, there is shown a link, associating such subsets with one another, and labelled with a percentage. The percentage represents the portion of the products from the earlier reaction stage to be reacted with the synthons in a subsequent reaction stage. For example, link 504 indicates that 50% of the products of R1 will be reacted with the subset of R2 that contains R2.1, R2.2, R2.3. Similarly, each of the contributions R2.1, R2.2, and R2.3 in FIG. 5F is labelled with a percentage representing the further allocation of the products from link 504 to the reactions with R2.1, R2.2, and R2.3 (i.e., 25%, 35%, and 40%, respectively). The computer used to generate and store representations of the combinatorial libraries may also store the values associated with each link and each further allocation. Thus, when the tags identifying a resulting molecule are input, the computer can determine the molecule's chemical structure and the combinatorial method used to generate the molecule.

The aforementioned description permits the benefits of combinatorial chemistry to be utilized while avoiding the necessity of mixing every product resulting from a reaction stage with every synthon from the next stage, in equal amounts.

It is another object of the present invention to produce an accurate enumeration of the contents of small molecule combinatorial libraries generated on solid support. Our invention accounts for the fact that small molecule combinatorial chemistry was made feasible by the assignee's binary coding technique, and that this technique was initially developed for solid phase synthesis. For example, the fact that certain contributions need not bind with all of the compounds formed in previous stages in small molecule combinatorial chemistry performed on solid support had to be understood and accounted for. In solid phase chemistry, contributions which do not bind to a compound generated in a previous phase will be "washed away," meaning that the synthon will not attach to the solid support at all and thus will not be incorporated into certain compounds in the final combinatorial library. For example, when any of the last three structures of R2 in FIG. 5A is chosen as the contribution for R2, there will be no place for any of the substituents in R3 to attach, and consequently the substituents in R3 would be considered "washed away" and not included in the final library of compounds. This is in contradistinction to chemistry performed in solution, whereby unattached compounds will be present in the combinatorial library in "free floating" form. Our invention will not include free floating compounds in the representation of the library it generates when enumerating structures synthesized on solid support, since such compounds are not present in small molecule combinatorial libraries generated on solid support. Existing systems do not account for this or other differences between solid phase chemistry and chemistry performed in solution. Our system was designed to accurately enumerate any combinatorial library, including, but not limited to, all small molecule combinatorial libraries generated on solid support.

Thus, with reference to FIG. 5A, it is noted that molecules containing any of the last three potential contributions shown for reaction stage R2 cannot attach to any contribution in reaction stage R3 because none of these last three R2 contributions includes an attachment point labeled "5," while a review of all six potential contributions in R3 shows that none of them includes attachment points labeled "1" or "2". Accordingly, any structure resulting from a combination of an R1 contribution with one of the last three contributions of R2 cannot include a contribution from R3.

Consider the second contribution shown for R1 which could combine with the fifth contribution shown for R2. The resulting structure would include three rings, the first two being the alicyclic and aromatic moieties already present in the second contribution of R1, and the third ring resulting from the attachment, at points labeled "1" and "2," of the fifth contribution in R2 to the carbon atom with labels "1" and "2" in the second contribution of R1. The resulting molecule has attachment points "3" and "4", which could serve to form a fourth ring with the first contribution of R4. However, the reaction stage R3 is effectively skipped because, although the molecules resulting from reaction stage R2 are physically mixed with the contributing synthons of R3, no chemical reaction can take place.

Furthermore, a contribution in a stage may actually be two or more unattached compounds, a possibility which we account for in our representation scheme by separating unattached compounds with a "*". For example, the last structure of R2 in FIG. 5A:

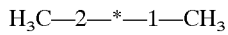

$H_3C$—2—*—1—$CH_3$ represents that a $CH_3$ group is to be attached at both position numbers "1" and "2" of the structures from stage 1. Any number of unattached compounds can be represented in a structure by depicting these as attached to the "*" or by using multiple "*'s".

It is another object of the present invention to provide a tool for tracking the contents of small molecule combinatorial libraries generated with binary coding. Applicants have discovered, by use of assignee's proprietary binary coding technique, that such a tool is necessary if large libraries of small molecules are to be successfully managed and tracked, and have invented a system and method for managing and tracking such libraries. This system and method has the capabilities of:

1) encompassing within the representation of each contribution a representation of the tag or tags associated with the synthon making such contribution;

2) inputting into the system the representation of a tag or tags (as well as identification of a library if the system contains more than one library) and outputting to the user a representation of the contribution made by the synthon associated with the tag or tags;

3) inputting into the system the representation of a tag or tags (as well as identification of a library if the system contains more than one library) and outputting to the user a representation of the synthesized compound or compounds produced on the solid support to which such tags are bound.

These features are described seriatim.

FIGS. 5B–5E show a representation of the same small molecule combinatorial library depicted in FIG. 5A, but include with the representation of each contribution the tags associated with such contribution. As shown in FIGS. 5B–5E, for example, the numbers immediately following the "R" (hereinafter referred to as the "R number") uniquely identify each potential contribution, with the number preceding the period indicating the stage and the number following the period indicating the substituent chosen from that stage. Thus, "R1.2" indicates the second member of the set of potential contributions from stage 1, "R2.5" the fifth member of the set of potential contributions from stage 2, and so on. The actual names of the contributing synthons or definitions of the chemistry by which they were created are not included in a preferred embodiment because they are not necessary in order to view and understand the contents of a small molecule combinatorial library. However, those skilled in the relevant art will appreciate that the names of the contributing synthons or definitions of the chemistry by which they were created could just as easily be included in the representations shown in FIGS. 5B–5E if they are considered relevant or useful.

Following the R number is a colon, after which a list of the tags associated with the contributing synthon appear, separated by semicolons. Tags are "associated" in the present invention by virtue of the fact that presence of a tag implies presence of the contribution from a particular synthon. The association can be physically maintained by simply indicating, in a computer, which tags imply the presence of which molecules.

In a preferred embodiment, the tags are identified by distinguishing characteristics of the tagging molecules. For example, "C10 C15" refers to a tagging molecule which has ten carbon and five chlorine atoms. However, those skilled in the relevant art will appreciate that any method can be used for identifying the tags associated with a contributing synthon, and all fall within the scope of the present invention.

The present invention also includes an input device into which the tag or tags associated with a contributing synthon can be entered, and an output device onto which the corresponding contribution can then be displayed. Similarly, the present invention provides for entry of a contributing synthon identifier, which will cause the tag or tags associated with the contributing synthon to be displayed. While, in a preferred embodiment, the format in which tags and contributions or contributing synthons are entered and/or displayed are as shown in FIGS. 5B–5E, those skilled in the relevant art will appreciate that any method for entering and/or displaying this information can be used, and the present invention should not be deemed to be limited by any method and/or medium for entry and/or display of tag or synthon information.

The present invention also includes an input device into which can be entered a representation of the tag or tags bound to the solid support on which a combinatorial library member was synthesized, which will cause to be displayed the chemical structure of that library member. In a preferred embodiment, the tag or tags bound to the solid support are entered using distinguishing characteristics of the tagging molecules as illustrated in FIGS. 5A–5E, and the display used for a library member is its actual chemical structure. However, those skilled in the relevant art will appreciate that any method and/or medium can be used to enter the tag information or to display the library member information, and the present invention should not be deemed to be limited by any method and/or medium for entry of tag information and/or display of library member information.

Figure 6:
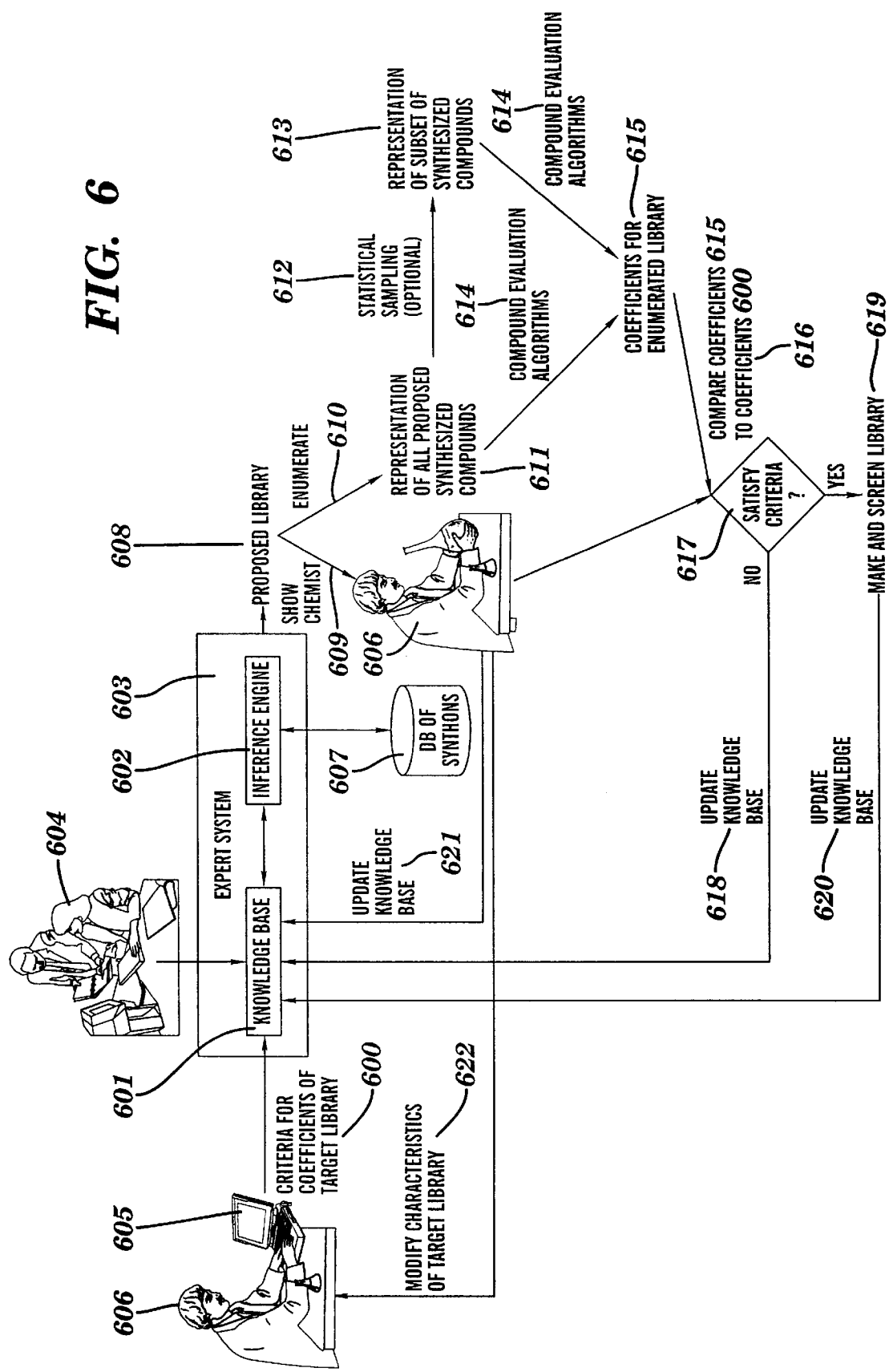
FIG. 6 illustrates the operation of a preferred embodiment of the starting molecule selection method and apparatus of the instant invention.

It is another object of the present invention to provide a small molecule combinatorial library planning tool for automatically and intelligently selecting synthons without performing a chemical synthesis. In a preferred embodiment, this is achieved by utilizing an expert system for which the criteria used by scientists to select synthons serves as the initial knowledge base, although those skilled in the art will recognize that any computational system can be utilized. FIG. 6 shows the components and steps which make up this aspect of the present invention.

As is understood by those skilled in the relevant art, a knowledge base contains rules and facts which are used by the expert system to draw conclusions. The knowledge base of the instant invention, depicted in FIG. 6, contains rules and facts to be applied in the selection of synthons. The knowledge base of a preferred embodiment of the present invention is initialized with rules obtained from subject matter experts.

Table 1 contains a partial list of compound characteristics which typically are used by chemists to select synthons, along with brief comments regarding the application of each characteristic. For example, if a combinatorial library of lipophilic compounds is desired, synthons which are lipophilic will be selected. Methods for calculating lipophilicity are described in the Martin et al. article incorporated by reference hereinabove. These and other rules regarding the types of synthons to select in order to obtain given characteristics in the target library are incorporated into the knowledge base of the present invention. Those skilled in the relevant art will appreciate that many different rules can be incorporated into the knowledge base, and the scope of the present invention is not limited to a knowledge base containing any one or more rules.

TABLE 1

| | |
|---|---|
| Lipophilicity | (in general a desirable range for the lipophilicity of finished compounds is between 0 and 5) |
| Hydrogen Bonding Ability | (measured by the number of heteroatoms) |
| Molecular Weight | (the molecular weight of the most preferred finished compounds is less than 700) |
| Diversity of Atom Descriptors | (a library of finished compounds should not be concentrated in a particular class along any of the commonly used atom-pair or atom-torsion descriptors, but rather should make up a diverse set) |
| Polyaromatics | (are generally undesirable in a library of finished compounds because they are considered to be cancer-causing agents) |
| Anilines | (are generally undesirable in a library of finished compounds because they are typically toxic) |

As shown in FIG. 6, scientists 604 generate the rules with which the knowledge base 601 of the expert system 603 is initialized. Two rules which might be included in the knowledge base are expressed as Rules 1 and 2 below. These rules are written in pseudocode, but those skilled in the relevant art will appreciate that these rules can be easily translated into the syntax of any of the commercially available expert system shells, expert system toolkits or programming languages with which rules can be represented:

```
/* Rule 1 */
IF (target library lipophilicity ≧ X) THEN select synthons whose
lipophilicity ≧ f(X)
/* Rule 2 */
f(X) = X
```

Using Rules 1 and 2, if a scientist wants a combinatorial library created with compounds having a lipophilicity of X or greater, synthons will be selected whose lipophilicity is greater than or equal to some function of X, where this function of X is defined by Rule 2 to be equal to X itself. Referring again to FIG. 6, the lipophilicity criteria of the target library are selected by chemist 606, and are entered into the expert system via input device 605, which in a preferred embodiment is a computer or a computer terminal.

Inference engine 602, as will be readily understood by those skilled in the relevant art, is the control module of the expert system. It reads the rules in the knowledge base and forms conclusions and takes actions based thereon. Thus, if Rules 1 and 2 above were the only rules in the knowledge base, inference engine 602 would read these rules and select from the database of synthons 607 all which have a lipophilicity of greater than or equal to the value X selected by chemist 606. Similar rules and techniques can be used to select the contributions desired from subsequent stages.

Using techniques and criteria such as those described, a proposed library 608 is automatically generated by the expert system 603. This library can be represented as a set of synthons for stage 1 and synthons for stages 2–N. Alternatively, the library can be represented as the contributions possible from each stage of the synthesis. Those skilled in the relevant art will appreciate that many different techniques and criteria can be used to generate a representation of the proposed library, and this aspect of the present invention is not limited to any one or more techniques or criteria.

Although the format for representing the proposed library can vary, in a preferred embodiment the representation used is that which we developed, described above, for concisely representing the contents of small molecule combinatorial chemistry libraries. One reason for use of our library representation with this aspect of the invention in a preferred embodiment is that it can be shown to a chemist 606 who, based on a visual inspection of same, can quickly evaluate whether the library has the desired characteristics. If the library does not, the chemist can evaluate whether the rule base needs to be modified and, if so, it may be modified accordingly as shown in step 621. Alternatively, the chemist may decide the rules are satisfactory, but that the characteristics of the target library should be modified. In this case, he can define new characteristics and enter them into the expert system 603 via input device 605 as shown in step 622.

As shown in FIG. 6, the present invention also contemplates evaluating the proposed library automatically. In a preferred embodiment, in which our library representation is used, the enumeration component of that aspect of the invention is used to enumerate the proposed library in step 610 of FIG. 6. This causes a representation of all proposed synthesized compounds 611 to be automatically generated.

The representation of all proposed synthesized compounds can then optionally be statistically sampled, as shown at step 612 of FIG. 6. This statistical sampling will produce a subset 613 of the representations of all the proposed synthesized compounds 611. This statistical sampling can be performed automatically using any sampling methodologies, including but not limited to random sampling. The advantage of employing statistical sampling is that, by reducing the number of compound representations on which the compound evaluation algorithms 614 must be run, the computational resources required by such compound evaluation algorithms is reduced.

The compound evaluation algorithms 614 utilize known computational methods for measuring characteristics of compounds, such as those identified in Table 1. Examples of such computational methods are described in the Martin et al. reference incorporated by reference hereinabove, although those skilled in the relevant art will recognize that other such computational methods exist, and that the present invention is not limited to use of the methods described in the Martin et al. reference. These algorithms generate coefficients for the enumerated library 615 which are compared in step 616 to the criteria 600 (e.g., diversity) defined for the coefficients of the target library. If the coefficients for the enumerated library do not satisfy the criteria defined for the coefficients of the target library when they are compared in step 616, the rules of the knowledge base are updated as shown in step 618 to reflect the information learned from the results of the compound evaluation algorithms. For example, if the lipophilicity of the target library was defined to be 2 or greater and the lipophilicity of the enumerated library is 1, the lipophilicity of the synthons utilized must be increased. One way to do this would be to modify Rule 2 in the example above to make f(X) greater than X, e.g., f(X)=X+1.

If the coefficients for the enumerated library do satisfy the criteria defined for the coefficients of the target library, the library represented is made and screened as shown in step 619. This testing of the synthesized library for desirable properties will itself provide information with which the rules of the knowledge base can be updated as shown in step 620. These rules will include those which relate enumerated library coefficients to target properties. For example, it may be learned that synthesized compounds with a high lipophilicity uniformly or with great regularity provide hits against certain biological targets. This information can, either automatically or manually, be incorporated into the rules of the knowledge base such that scientists defining the target characteristics of other libraries would need to identify only the target to be screened, and the expert system would be able not only to deduce that such characteristics as lipophilicity are applicable to that target, but also to apply the relevant lipophilicity criteria which have previously produced hits for that target. Such criteria would be utilized, inter alia, by the system in the selection of synthons for the generation of a library containing molecules having the desired characteristics.

We claim:

1. An apparatus for representation of members of a combinatorial chemistry library comprising:
    a) means for identifying each potential synthon for each reaction stage in a combinatorial reaction series;
    b) means for identifying the contribution made, respectively, by each potential synthon identified in a), that is, the portion of the potential synthon which ultimately could be incorporated into a member of the combinatorial chemistry library;
    c) means for indicating for each contribution identified in b), every position at which the contribution may attach to another contribution made by another synthon utilized in a previous or subsequent reaction stage;
    d) means for specifying a label for each position indicated in c), wherein a particular contribution can attach to a previous or subsequent contribution at any position having the same label on both the particular contribution and the previous or subsequent contribution; and
    e) means for dividing the contributions from at least one reaction stage into subsets, wherein at least one of the subsets is not to be combined with a contribution from a previous or subsequent reaction stage.

2. The apparatus of claim 1, further comprising means for identifying one or more tags which uniquely identify the contribution made by each potential synthon.

3. The apparatus of claim 2, further comprising means for identifying said potential synthon based on the identities of said one or more tags.

4. The apparatus of claim 1, wherein said label comprises a number, representing a potential bond.

5. The apparatus of claim 1, further comprising:
    f) means for enumerating said representation by attaching, at a labeled position of attachment specified in d), a contribution from a particular reaction stage to a position of attachment having the same label on a contribution from a previous or subsequent reaction stage, and repeating said attaching until there are no labeled positions that have not been attached to another labeled position, so as to represent the entire chemical structure of a member of said combinatorial chemistry library.

6. The apparatus of claim 5 wherein said means for enumerating said representation comprises means for omitting any and all unattached contributions, that is, any contribution having no labeled position for attachment to another contribution from a previous or subsequent contribution.

7. The apparatus of claim 1, wherein said label comprises a letter, representing a potential bond.

8. A computer-implemented method for representation of members of a combinatorial chemistry library, the method comprising the steps of:
    a) identifying each potential synthon for each reaction stage in a combinatorial reaction series;
    b) identifying the contribution made, respectively, by each potential synthon identified in step a), that is, the portion of the potential synthon which ultimately could be incorporated into a member of the combinatorial chemistry library;
    c) indicating, for each contribution identified in step b), every position at which the contribution may attach to another contribution made by another synthon utilized in a previous or subsequent reaction stage;
    d) specifying a label for each position indicated in step c), wherein a particular contribution can attach to a previous or subsequent contribution at any position having the same label on both the particular contribution and the previous or subsequent contribution; and
    e) dividing the contributions from at least one reaction stage into subsets, wherein at least one of the subsets is not to be combined with a contribution from a previous or subsequent reaction stage.

9. The computer-implemented method of claim 8, wherein the contribution identified in step b) contains more than two positions for attachment to contributions from previous or subsequent reaction stages.

10. The computer-implemented method of claim 8, wherein said combinatorial chemistry library is encoded with tags and said method further comprises identifying, for each contribution, one or more tags which uniquely identify such contribution.

11. The computer-implemented method of claim 8, wherein said label comprises a number, representing a potential bond.

12. The computer-implemented method of claim 8, further comprising:

f) enumerating said representation by attaching, at a labeled position of attachment specified in step d), a contribution from a particular reaction stage to a position of attachment having the same label on a contribution from a previous or subsequent reaction stage, and repeating said attaching until there are no labeled positions that have not been attached to another labeled position, so as to represent the entire chemical structure of a member of said combinatorial chemistry library.

13. The computer-implemented method of claim 8, wherein said label comprises a letter, representing a potential bond.

\* \* \* \* \*